US00RE41595E

(19) United States
(12) Reissued Patent
Shandle et al.

(10) Patent Number: US RE41,595 E
(45) Date of Reissued Patent: Aug. 31, 2010

(54) ANTIBODY PURIFICATION

(75) Inventors: Paul J. Shandle, Lafayette, CA (US); John C. Erickson, King of Prussia, PA (US); Robert G. Scott, King of Prussia, PA (US); Thomas M. Smith, King of Prussia, PA (US)

(73) Assignee: GlaxoSmithKline LLC, Philadelphia, PA (US)

(21) Appl. No.: 12/403,799

(22) Filed: Mar. 13, 2009

Related U.S. Patent Documents

Reissue of:
(64) Patent No.: 5,429,746
Issued: Jul. 4, 1995
Appl. No.: 08/200,126
Filed: Feb. 22, 1994

U.S. Applications:
(63) Continuation of application No. 11/804,729, filed on May 18, 2007, which is a continuation of application No. 11/140,525, filed on May 27, 2005, now Pat. No. Re. 40,070.

(51) Int. Cl.
*B01D 15/08* (2006.01)
*B01D 15/32* (2006.01)
*C07K 16/00* (2006.01)
*C07K 1/00* (2006.01)

(52) U.S. Cl. ..... 210/635; 210/656; 530/387.1; 530/390.5; 530/413; 530/417

(58) Field of Classification Search ..... 210/198.2, 210/635, 656; 530/387.1, 390.5, 413, 417
See application file for complete search history.

(56) References Cited

U.S. PATENT DOCUMENTS 4,639,513 A * 1/1987 Hou et al. ..... 530/390.5
4,983,722 A 1/1991 Bloom et al. ..... 530/387.1
5,115,101 A * 5/1992 Bloom et al. ..... 530/388.25
5,122,373 A * 6/1992 Eibl et al. ..... 424/177.1
5,164,487 A 11/1992 Kothe et al. ..... 530/389.1
5,190,752 A * 3/1993 Moller et al. ..... 424/176.1
5,219,999 A * 6/1993 Suzuki et al. ..... 530/390.5
5,252,216 A * 10/1993 Folena-Wasserman et al. ..... 210/635
5,268,306 A * 12/1993 Berger et al. ..... 436/527
5,571,720 A * 11/1996 Grandics et al. ..... 435/286.1

FOREIGN PATENT DOCUMENTS

| | | | |
|---|---|---|---|
| JP | A-2-084193 | | 3/1990 |
| JP | A-6-501152 | | 2/1994 |
| WO | WO 92/02049 | * | 2/1991 |
| WO | WO92/04381 | | 3/1992 |
| WO | WO93/02108 | | 2/1993 |

OTHER PUBLICATIONS

Whatman web article (Mar. 2007).*
Hakalahti, et al., "Purification of monoclonal antibodies raised against prostate acid phosphatase for use in vivo in radioimaging of prostatic cancer," *Journal of Immunological Methods*(1989) 117:131–136.
Abe, et al., "Purification of monoclonal antibodies with light–chain heterogeneity produced by mouse hybridomas raised with NS–1 myelomas: application of hydrophobic interaction high–performance liquid chromatography," *Journal of Biochemical and Biophysical Methods* (1993) 27:215–227.
Danielsson, et al., "One–step purification of monoclonal IgG antibodies from mouse ascites," *Journal of Immunological Methods* (1988) 115:79–88.

* cited by examiner

*Primary Examiner*—John Kim
(74) *Attorney, Agent, or Firm*—Andrea V. Lockenour; William T. Han; Edward R. Gimmi

(57) ABSTRACT

This invention relates to the application of hydrophobic interaction chromatography combination chromatography to the purification of antibody molecule proteins.

4 Claims, 1 Drawing Sheet

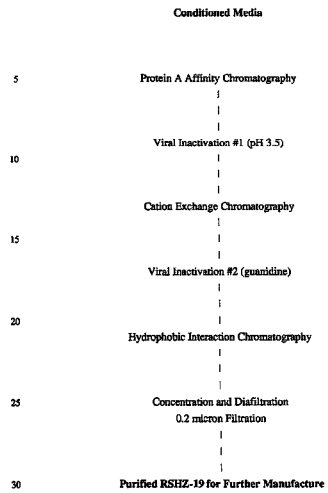

Conditioned Media

Protein A Affinity Chromatography

|

|

|

Viral Inactivation #1 (pH 3.5)

|

|

|

Cation Exchange Chromatography

|

|

|

Viral Inactivation #2 (guanidine)

|

|

|

Hydrophobic Interaction Chromatography

|

|

|

Concentration and Diafiltration 0.2 micron Filtration

|

|

|

Purified RSHZ-19 for Further Manufacture

FIGURE 1

ANTIBODY PURIFICATION

Matter enclosed in heavy brackets [ ] appears in the original patent but forms no part of this reissue specification; matter printed in italics indicates the additions made by reissue.

*More than one reissue application has been filed for the reissue of U.S. Pat. No. 5,429,746. The reissue applications are application Ser. No. 12/403,799 (the present reissue) which is a continuation of the reissue application Ser. No. 11/804,729 filed May 18, 2007, which is a continuation of the reissue application Ser. No. 11/140,525, filed May 27, 2005 now U.S. Pat. No. RE40,070.*

FIELD OF THE INVENTION

This invention relates to the field of protein purification. More specifically, this invention relates to the application of Hydrophobic Interaction Chromatography (HIC) to the separation of Immunoglobulin G monomers and to the integration of HIC into a combination chromatographic protocol for the purification of IgG antibody molecules.

BACKGROUND OF THE INVENTION

Historically, protein purification schemes have been predicated on differences in the molecular properties of size, charge and solubility between the protein to be purified and undesired protein contaminants. Protocols based on these parameters include size exclusion chromatography, ion exchange chromatography, differential precipitation and the like.

Size exclusion chromatography, otherwise known as gel filtration or gel permeation chromatography, relies on the penetration of macromolecules in a mobile phase into the pores of stationary phase particles. Differential penetration is a function of the hydrodynamic volume of the particles. Accordingly, under ideal conditions the larger molecules are excluded from the interior of the particles while the smaller molecules are accessible to this volume and the order of elution can be predicted by the size of the protein because a linear relationship exists between elution volume and the log of the molecular weight.

Chromatographic supports based on cross-linked dextrans e.g. SEPHADEX®, spherical agarose beads e.g. SEPHAROSE® (both commercially available from Pharmacia AB. Uppsala, Sweden), based on cross-linked polyacrylamides e.g. BIO-GEL® (commercially available from Bio-Rad Laboratories, Richmond, Calif.) or based on ethylene glycol-methacrylate co-polymer e.g. TOYOPEARL HW65 (commercially available from Toso Haas Co., Tokyo, Japan) are useful in forming the various chromatographic columns for size exclusion, or HIC chromatography in the practice of certain aspects of this invention.

Precipitation methods are predicated on the fact that in crude mixtures of proteins the solubilities of individual proteins are likely to vary widely. Although the solubility of a protein in an aqueous medium depends on a variety of factors, for purposes of this discussion it can be said generally that a protein will be soluble if its interaction with the solvent is stronger than its interaction with protein molecules of the same or similar kind. Without wishing to be bound by any particular mechanistic theory describing precipitation phenomena, it is nonetheless believed that interaction between a protein and water molecules can occur by hydrogen bonding with several types of uncharged groups and/or electrostatically, as dipoles, with charged groups and that precipitants such as salts of monovalent cations (e.g. ammonium sulfate) compete with proteins for water molecules. Thus at high salt concentrations, the proteins become "dehydrated" reducing their interaction with the aqueous environment and increasing the aggregation with like or similar proteins, resulting in precipitation from the medium.

Ion exchange chromatography involves the interaction of charged functional groups in the sample with ionic functional groups of opposite charge on an adsorbent surface. Two general types of interaction are known. Anionic exchange chromatography is mediated by negatively charged amino acid side chains (e.g., aspartic acid and glutamic acid) interacting with positively charged surfaces and cationic exchange chromatography is mediated by positively charged amino acid residues (e.g., lysine and arginine) interacting with negatively charged surfaces.

More recently affinity chromatography and hydrophobic interaction chromatography techniques have been developed to supplement the more traditional size exclusion and ion exchange chromatographic protocols. Affinity chromatography relies on the specific interaction of the protein with an immobilized ligand. The ligand can be specific for the particular protein of interest in which case the ligand is a substrate, substrate analog, inhibitor, receptor or antibody. Alternatively, the ligand may be able to react with a number of related proteins. Such group specific ligands as adenosine monophosphate, adenosine diphosphate, nicotine adenine dinucleotide or certain dyes may be employed to recover a particular class of proteins.

With respect to the purification of antibody molecules, both specific and generalized affinity techniques are applicable. The most specific choice of ligand for the affinity purification of an antibody is the antigen (or an epitope thereof) to which desired antibody reacts. Many of the well-known immunosorbent assays such as the enzyme-linked immunosorbent assays (ELISA) are predicated on such specific antigen/antibody affinity interactions.

However, generalized affinity techniques are also useful. For example, Staphylococcal Protein A is known to bind certain antibodies of the IgG class (See: Ey, P. L. et al. Immunochemistry 15:429–36 (1978)). Alternatively, antisera raised in heterologous species (e.g. rabbit anti-mouse antisera) can be used to separate general groups of antibodies. (See, Current Protocols in Molecular Biology Supra, Chap. 11.)

Hydrophobic interaction chromatography was first developed following the observation that proteins could be retained on affinity gels which comprised hydrocarbon spacer arms but lacked the affinity ligand. Although in this field the term hydrophobic chromatography is sometimes used, the term hydrophobic interaction chromatography (HIC) is preferred because it is the interaction between the solute and the gel that is hydrophobic not the chromatographic procedure. Hydrophobic interactions are strongest at high ionic strength, therefore, this form of separation is conveniently performed following salt precipitations or ion exchange procedures. Elution from HIC supports can be effected by alterations in solvent, pH, ionic strength, or by the addition of chaotropic agents or organic modifiers, such as ethylene or propylene glycol. A description of the general principles of hydrophobic interaction chromatography can be found in U.S. Pat. No. 3,917,527 and in U.S. Pat. No. 4,000,098. The application of HIC to the purification of specific proteins is exemplified by reference to the following disclosures: human growth hormone (U.S. Pat. No. 4,332,717), toxin conjugates (U.S. Pat. No. 4,771,128), antihemolytic factor (U.S. Pat. No. 4,743,680), tumor necrosis factor (U.S. Pat. No. 4,894,439), interleukin-2(U.S. Pat. No. 4,908,434), human lymphotoxin (U.S. Pat. No. 4,920,196) and lysozyme species (Fausnaugh, J. L. and F. E. Regnier, J. Chromatog. 359:131–146 (1986)) and soluble complement receptors (U.S. Pat. No. 5,252,216). HIC in the context of high performance liquid chromatography (HPLC) has been used to separate antibody fragmens (e.g., $F(ab')_2$) from intact antibody molecules in a single step protocol. (Morimoto, K. et al., J. Biochem. Biophys. Meth. 24:107–117 (1992)).

In addition to affinity and HIC techniques, one or more of the traditional protein purification schemes have been applied to antibody purification. For example, Hakalahti, L. et al., (J. Immunol. Meth. 117:131–136 (1989)) disclose a protocol employing two successive ion exchange chromatographic steps or one employing a single ion exchange step followed by a HIC step. Danielsson A. et al. (J. Immunol. Methods 115:79–88 (1988))compare single step protocols based on anion exchange, cation exchange, chromatofocusing and HIC respectively.

Although Protein A affinity column chromatography is widely used, it is also appreciated that elution of antibody from such columns can result in leaching of residual Protein A from the support. Size exclusion HPLC (Das et al., Analytical Biochem, 145:27–36 (1985)) an anion exchange chromatography (EPO345549, published Dec. 13, 1989) have been suggested as means for dealing with this problem.

It has now been surprisingly discovered that HIC can be usefully employed to remove contaminating Protein A from IgG mixtures eluted from Protein A chromatographic support.

This invention relates to the application of HIC to the separation of monomeric IgG from mixtures containing same and to the integration of HIC into a protocol combining Protein A and ion exchange chromatography for the purification of immunoglobulin G molecules.

BRIEF DESCRIPTION OF THE INVENTION

This invention relates to a method for separating IgG monomers from aggregates in mixtures containing same by contacting said mixture with a hydrophobic interaction chromatographic support and selectively eluting the monomer from the support.

In another aspect the invention provides for the purification of an IgG antibody from conditioned cell culture medium containing same comprising sequentially subjecting the medium to (a) Protein A, (b) ion exchange chromatography, and (c) hydrophobic interaction chromatography.

In another aspect the invention provides a method for removing Protein A from a mixture comprising Protein A and antibodies comprising contacting said mixture with a hydrophobic interaction chromatography support and selectively eluting the antibody from the support.

DETAILED DESCRIPTION OF THE FIGURES

FIG. 1 illustrates a flow diagram of one process for purifying an antibody according to this invention.

DETAILED DESCRIPTION OF THE INVENTION

This invention relates to protein purification techniques which have application to the large scale purification of immunoglobulin molecules. The invention is particularly useful because it permits the recovery of monomeric IgG of >95% protein purity. The invention may be applied to the purification of a number of different immunoglobulin G molecules.

Antibody-like proteins are proteins which may be purified by the protocol described herein, such protocol being modified if necessary by routine, non-inventive adjustments that do not entail undue experimentation. Such proteins include isotypes, allotypes and alleles of immunoglobulin genes, truncated forms, altered antibodies, such as chimeric antibodies, humanized antibodies and the like, chemically modified forms such as by PEG treatment, and fusion proteins containing an immunoglobulin moiety. These proteins are referred to as antibody-like because they possess or retain sufficient immunoglobulin protein properties (e.g. $F_c$ determinants) to admit to purification by the process of this invention. Unless specifically identified otherwise, the term antibody or immunoglobulin protein also includes antibody-like proteins.

The immunoglobulin molecules of this invention can be isolated from a number of sources, including without limitation, serum of immunized animals, ascites fluid, hybridoma or myeloma supernatants, conditioned media derived from culturing a recombinant cell line that expresses the immunoglobulin molecule and from all cell extracts of immunoglobulin producing cells. This invention is particularly useful for the purification of antibodies from conditioned cell culture media of a variety of antibody producing recombinant cell lines. Although one may expect some variation from cell line to cell line and among the various antibody products, based on the disclosure herein, it is well within the purview of one of ordinary skill in this an to adapt the invention herein to a particular combination of antibody protein and producing cell line.

Generally, genes encoding proteins such as antibodies may be cloned by incorporating DNA sequences coding for the desired regions of the polypeptide into a recombinant DNA vehicle (e.g., vector) and transforming or transfecting suitable prokaryotic or eukaryotic hosts. Suitable prokaryotic hosts include but are not limited to Escherichia, Streptomyces, Bacillus and the like. Suitable eukaryotic hosts include but are not limited to yeast, such as Saccharomyces and animal cells in culture such as VERO, HeLa, mouse C127, Chinese hamster ovary (CHO), WI-38, BHK, COS, MDCK, myeloma, and insect cell lines. Particularly preferred hosts are CHO cell lines deficient in dihydrofolate reductase such as ATCC CRL 1793, CRL 9096 and other cell lines described herein below. Such recombinant techniques have now become well known and are described in Methods in Enzymology, (Academic Press) Volumes 65 and 69 (1979), 100 and 101 (1983), and the references cited therein. An extensive technical discussion embodying most commonly used recombinant DNA methodologies can be found in Maniatis, et al., Molecular Cloning, Cold Spring Harbor Laboratory (1982) or Current Protocols in Molecular Biology, Greene Publishing, Wiley Interscience (1988, 1991, 1993).

One way of obtaining a DNA fragment encoding a desired polypeptide such as an antibody molecule is via cDNA cloning. In this process, messenger RNA (mRNA) is isolated from cells known or suspected of producing the desired protein. Through a series of enzymatic reactions, the mRNA population of the cells is copied into a complementary DNA (cDNA). The resulting cDNA is then inserted into cloning vehicles and subsequently used to transform a suitable prokaryotic or eukaryotic host. The resulting cDNA "library" is comprised of a population of transformed host cells, each of which contain a single gene or gene fragment. The entire library, in theory, provides a representative sample of the coding information present in the mRNA mixture used as the starting material. The libraries can be screened using nucleic acid or antibody probes in order to identify specific DNA sequences. Once isolated, these DNA sequences can be modified or can be assembled into complete genes.

Specific fragments of an antibody gene can be engineered independently of the rest of the gene. DNA fragments encoding Complementarity Determining Regions (CDRs) can be integrated into DNA frame-work sequences from heterologous species to yield altered antibodies. These altered antibodies have significant utility in the treatment of undesirable physiological conditions. For example, PCT/GB91/01554 (published as WO92/04381) discloses the production of "humanized" antibodies useful for the treatment and prevention of Respiratory Syncytial Virus (RSV) infection. Alternatively, the entire variable region of antibody gene can be fused to the constant domain of a second antibody to form an altered antibody otherwise known as a "chimeric antibody". For example, PCT/US92/06194 (published as WO93/02108) discloses a monkey/human chimeric antibody reactive with the human CD4 receptor.

Once the antibody gene or gene fragment has been cloned, the DNA may be introduced into an expression vector and that construction used to transform an appropriate host cell. An expression vector is characterized as having expression control sequences as defined herein, such that when a DNA sequence of interest is operably linked thereto, the vector is capable of directing the production of the product encoded by the DNA sequence of interest in a host cell containing the vector. With specific reference to this invention, it is possible to assemble fragments of a single coding sequence such that upon expression an antibody molecule is formed. A particularly efficacious application of this protocol to recombinant antibody production is found in the Harris, et al. PCT Applications WO92/04381, published Mar.19, 1992, cited above, and in the Newman et al. PCT Application WO93/02108, published Feb. 4, 1993, cited above.

After the recombinant product is produced it is desirable to recover the product. If the product is exported by the cell producing it, the product can be recovered directly from the cell culture medium. If the product is retained intracellularly, the cells must be physically disrupted by mechanical, chemical or biological means in order to obtain the intracellular product.

In the case of a protein product, the purification protocol should not only provide a protein product that is essentially free of other proteins, by which is meant at least 80% and preferably greater than 95% pure with respect to total protein in the preparation, but also eliminate or reduce to acceptable levels other host cell contaminants, DNA, RNA, potential pyrogens and the like. Furthermore, in the context of antibody production by recombinant expression system, it is appreciated that aggregation of the 150,000 dalton IgG product into higher molecular weight species can occur. Accordingly, for purposes of product purity and standardization it is also useful to separate the native 150,000 dalton monomeric species from higher molecular weight aggregates and other misfolded forms. While it is appreciated that the 150,000 dalton IgG species is composed of four polypeptide chains (2 heavy chains and 2 light chains), the 150,000 dalton species is referred to herein as a "monomer" or "monomeric IgG".

As mentioned above, a variety of host cells may be used for the production of the antibodies of this invention. The choice of a particular host cell is well within the purview of the ordinary skilled artisan taking into account, inter alia, the nature of the antibody, its rate of synthesis, its rate of decay and the characteristics of the recombinant vector directing the expression of the antibody. The choice of the host cell expression system dictates to a large extent the nature of the cell culture procedures to be employed. The selection of a particular mode of production, be it batch or continuous, spinner or air lift, liquid or immobilized can be made once the expression system has been selected. Accordingly, fluidized bed bioreactors, hollow fiber bioreactors, roller bottle cultures, or stirred tank bioreactors, with or without cell microcarriers may variously be employed. The criteria for such selection are appreciated in the cell culture art. They are not detailed herein because they are outside the scope of this invention. This invention relates to the purification of antibodies given their existence in a conditioned cell culture medium, hybridoma supernatant, antiserum, myeloma supernatant or ascites fluid.

As mentioned above this invention relates, inter alia, to application of hydrophobic interaction chromatography (HIC) to the separation and purification of antibody molecules. Hydrophobic molecules in an aqueous solvent will self-associate. This association is due to hydrophobic interactions. It is now appreciated that macromolecules such as proteins have on their surface extensive hydrophobic patches in addition to the expected hydrophilic groups. HIC is predicated, in part, on the interaction of these patches with hydrophobic ligands attached to chromatographic supports. A hydrophobic ligand coupled to a matrix is variously referred to herein as an HIC support, HIC gel or HIC column. It is further appreciated that the strength of the interaction between the protein and the HIC support is not only a function of the proportion of non-polar to polar surfaces on the protein but by the distribution of the non-polar surfaces as well and the chemistry of the HIC support.

A number of chromatographic supports may be employed in the preparation of HIC columns, the most extensively used are agarose, silica and organic polymer or co-polymer resins. Useful hydrophobic ligands include but are not limited to alkyl groups having from about 2 to about 8 carbon atoms, such as a butyl, propyl, or octyl; or aryl groups such as phenyl. Conventional HIC products for gels and columns may be obtained commercially from suppliers such as Pharmacia LKB AB, Uppsala, Sweden under the product names butyl-SEPHAROSE®, phenyl or butyl-SEPHAROSE® CL-4B, butyl-SEPHAROSE® FF, octyl-SEPHAROSE® FF and phenyl-SEPHAROSE® FF; Tosoh Corporation, Tokyo, Japan under the product names TOYOPEARL ether 650, phenyl 650 or butyl 650 (Fractogel); Miles-Yeda, Rehovot, Israel under the product name alkyl-agarose, wherein the alkyl group contains from 2–10 carbon atoms, and J. T. Baker, Phillipsburg, N.J. under the product name Bakerbond WP-HI-propyl.

It is also possible to prepare the desired HIC column using conventional chemistry. (See: for example, Er-el. Z. et al. Biochem. Biophys. Res. Comm. 49:383 (1972)or Ulbrich, V. et al. Coll. Czech. Chem. Commum. 9:1466 (1964)).

Ligand density is an important parameter in that it influences not only the strength of the interaction but the capacity of the column as well. The ligand density of the commercially available phenyl or octyl phenyl gels is on the order of 40 μmoles/ml gel bed. Gel capacity is a function of the particular protein in question as well as pH, temperature and salt type and concentration but generally can be expected to fall in the range of 3–20 mg/ml of gel.

The choice of a particular gel can be determined by the skilled artisan. In general the strength of the interaction of the protein and the HIC ligand increases with the chain length of the alkyl ligands but ligands having from about 4 to about 8 carbon atoms are suitable for most separations. A phenyl group has about the same hydrophobicity as a pentyl group, although the selectivity can be quite different owing to the possibility of pi-pi orbital interaction with aromatic groups on the protein. Selectively may also be affected by the chemistry of the supporting resin.

Adsorption of the proteins to a HIC column is favored by high salt concentrations, but the actual concentrations can vary over a wide range depending on the nature of the protein and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{++}<Ca^{++}<Mg^{++}<Li^{+}<Cs^{+}<Na^{+}<K^{+}<Rb^{+}<NH_4^{+}$, while anions may be ranked in terms of increasing chaotropic effect as $PO_4^{--}<SO_4^{--}<CH_3COO^{-}<Cl^{-}<Br^{-}<NO_3^{-}<ClO_4^{-}<I^{-}<SCN^{-}$.

Accordingly, salts may be formulated that influence the strength of the interaction as given by the following relationship:

$$(NH_4)_2SO_4>Na_2SO_4>NaCl>NH_4Cl>NaBr>NaSCN$$

In general, salt concentrations of between about 0.75 and about 2M ammonium sulfate or between about 1 and 4M NaCl are useful.

The influence of temperature on HIC separations is not simple, although generally a decrease in temperature decreases the interaction. However, any benefit that would accrue by increasing the temperature must also be weighed against adverse effects such an increase may have on the stability of the protein.

Elution, whether stepwise or in the form of a gradient, can be accomplished in a variety of ways: (a) by changing the salt concentration, (b) by changing the polarity of the solvent or (c) by adding detergents. By decreasing salt concentration adsorbed proteins are eluted in order of increasing hydrophobicity. Changes in polarity may be affected by additions of solvents such as ethylene or propylene glycol or (iso) propanol, thereby decreasing the strength of the hydrophobic interactions. Detergents function as displacers of proteins and have been used primarily in connection with the purification of membrane proteins.

Although it has been discovered that HIC chromatography can be used alone to separate monomeric IgG (MW 150,000) from aggregates and misfolded species, as mentioned above, HIC is particularly useful when used in combination with other protein purification techniques. That is to say, it is preferred to apply HIC to mixtures that have been partially purified by other protein purification procedures. By the term "partially purified" is meant a protein preparation in which the protein of interest is present in at least 5 percent by weight, more preferably at least 10% and most preferably at least 45%. By the term "mixture" is meant the desired monomeric IgG antibody molecule in combination with undesirable contaminants such as, without limitation, one or more of: immunoglobulin aggregates, misfolded species, host cell protein, residue material from preceding chromatographic steps such as Protein A when employed. Accordingly, the application of HIC can also be appreciated in the context of an overall purification protocol for immunoglobulin proteins such as affinity purified monoclonal antibodies. It has been found to be useful, for example, to subject a sample of conditioned cell culture medium to partial purification prior to the application of HIC. By the term "conditioned cell culture medium" is meant a cell culture medium which has supported cell growth and/or cell maintenance and contains secreted product. A sample of such medium is subjected to one or more protein purification steps prior to the application of a HIC step. The sample may be subjected to affinity chromatography employing Staphylococcus Protein A as a first step. For example, PROSEP-A® (BioProcessing Ltd., U.K.) which consists of Protein A covalently coupled to controlled pore glass can be usefully employed. Other useful Protein A formulations are Protein A SEPHAROSE® Fast Flow (Pharmacia) and TOYO-PEARL 650M Protein A (TosoHaas). As a second step, ion exchange chromatography may be employed. In this regard various anionic or cationic substituents may be attached to matrices in order to form anionic or cationic supports for chromatography. Anionic exchange substituents include diethylaminoethyl(DEAE), quaternary aminoethyl(QAE) and quaternary amine(Q) groups. Cationic exchange substituents include carboxymethyl (CM), sulfoethyl(SE), sulfopropyl(SP), phosphate(P) and sulfonate(S). Cellulosic ion exchange resins such as DE23, DE32, DE52, CM-23, CM-32 and CM-52 are available from Whatman Ltd. Maidstone, Kent, U.K. SEPHADEX®-based and cross-linked ion exchangers are also known. For example, DEAE-, QAE-, CM-, and SP- SEPHADEX® and DEAE-, Q-, CM-and S-SEPHAROSE® and SEPHAROSE® Fast Flow are all available from Pharmacia AB. Further, both DEAE and CM derivitized ethylene glycolmethacrylate copolymer such as TOYOPEARL DEAE-650S or M and TOYOPEARL CM-650S or M are available from Toso Haas Co., Philadelphia, Pa. Because elution from ion exchange supports usually involves addition of salt and because, as mentioned previously, HIC is enhanced under increased salt concentrations, the introduction of a HIC step following an ionic exchange chromatographic step or other salt mediated purification step is particularly preferred. Additional purification protocols may be added including but not necessarily limited to further ionic exchange chromatography, size exclusion chromatography, viral inactivation, concentration and freeze drying.

For purposes of illustration only, this invention was applied to the purification of several antibodies of the IgG isotype. More specifically, to a humanized antibody useful for the treatment of RSV infection described by Harris et al.; 1992, Intl. Patent Publication Number WO92/04381, published Mar. 19, 1992 (hereinafter "RSHZ-19") and a chimeric antibody specifically reactive with the CD4 antigen described by Newman et al. Int'l Patent Publication Number WO93/02108, published Feb. 4, 1993 (hereinafter CH-CD4). The construction of recombinant systems for the production of RSHZ-19 and the CH-CD4 chimeric antibodies are detailed in the above mentioned PCT Applications, the contents of which are incorporated herein by reference for purpose of background and are summarized as follows.

An expression plasmid containing the RSHZ-19 coding sequence was cotransfected with pSV2dhfr into a dhfr-requiring Chinese Hamster Ovary cell line (CHO-DUXBII). The transfection was carried in growth medium and employed the calcium coprecipitation/glycerol shock procedure as described in: DNA Cloning, D. M. Glover ed. (Chap. 15, C. Gorman). Following transfection, the cells were maintained in growth medium for 46 hours under growth conditions (as described above) prior to the selection procedure.

The selection and co-amplification procedure was carried out essentially as described by R. J. Kaufman, et al.( Mol. Cell. Biol. 5:1750–1759 (1985)). Forty-six hours post transfection the cells were changed to selective medium MEM ALPHA (041-02571), 1% stock glutamine, 1% stock pen/strep (043-05070) and dialyzed bovine fetal calf serum (220-6300AJ) (Gibco, Paisley, Scotland). The cells were maintained in the selective medium for 8–10 days until dhfr+ colonies appeared. When the colonies were established the cells were changed into a selective medium containing methotrexate, (A6770, Sigma Chem. Co., St. Louis, Mo.). The methotrexate concentration was initially 0.02 μM and was increased stepwise to 5 μM. During the amplification procedure aliquots of growth medium from growing cells were assayed for RSHZ-19 production by human IgG. Any antibody secreting recombinant cell line may be used to supply the conditioned medium for purification according to this invention, a particular cell line certainly is not required.

A transfected CHO cell line capable of producing RSHZ-19 can be cultured by a variety of cell culture techniques. For the application of this invention the particular method of culturing is not critical.

As mentioned previously, the particular recombinant production system and the particular cell culturing protocol is outside the scope of this invention. The system and protocol discussed above are representative of the many options available to the skilled artisan and they are included herein for purposes of illustration only. The purification protocol which is the subject of this invention is applicable, with only routine modification, to a variety of recombinant antibodies and antibody-like proteins regardless of how they are produced or cultured. For example a chimeric monoclonal antibody to CD4 was also purified by the process of this invention.

The purified antibodies obtained by practicing the process of this invention have the following properties: 1) greater than 97% antibody protein by weight; 2) stable to proteolytic degradation at 4° C. for at least three months; 3) low (<0.1 E.U./mg protein) endo-toxin; 4) low (<1 pg/mg protein) DNA; 5) non-antibody protein <5% by weight; and 6) virally inactive. The following examples further illustrate this invention but are not offered by way of limitation of the claims herein.

EXAMPLE 1

INTRODUCTION

The procedure outlined below was developed for the isolation and purification of a monoclonal antibody against Respiratory Syncytial Virus (RSV). This antibody is a "humanized" IgG expressed in CHO cells, and grown in a stirred tank bioreactor. The antibody is more fully described in PCT WO92/04381 and is otherwise referred to herein as RSHZ 19. The process is designed to prepare RSHZ-19 of >95% purity while removing contaminants derived from the host cell, cell culture medium, or other raw materials. The process in its most preferred embodiment consists of three purification steps (Protein A affinity, cation exchange, and hydrophobic interaction chromatography), two viral inactivation steps, and a diafiltration step to exchange the product into a final buffer of choice (outlined in FIG. 1). All steps are carried out at room temperature (18°–25° C.). All buffers are prepared with WFI and filtered through either a 0.2 micron filter or a 10,000 MWCO membrane before use. Buffer formulations are listed in Table 1. Tables 2, 4, 6 and 8 show the column parameters for examples IA, IB, IC and ID respectively. Tables 3, 5 and 7 and 9 provide a purification summary for examples IA, IB, IC and ID respectively.

The first step in the process (Protein A affinity chromatography on ProSep A) can be rapidly cycled to accommodate varying amounts of cell-free culture fluid (CCF), and has a capacity of approximately 15 grams RSHZ-19 per liter of ProSep A. For example, 500 liters CCF containing 400–500 grams of IgG can be processed in 5 or 6 cycles. The downstream steps of the process (Cation Exchange Chromatography (CEC) and Hydrophobic Interaction Chromatography (HIC) are scaled to accommodate approximately 130–140 grams RSHZ-19 per cycle. Thus, a 500 liter culture containing 400–500 grams of RSHZ-19 is processed in three downstream cycles after capture of ProSep A.

The hydrophobic interaction chromatography step (HIC) has been demonstrated to remove residual Protein A that leaches from the Protein A column during elution (See: examples IA–D). In addition, aggregates of IgG can be removed over HIC, as shown in examples IC and ID.

The process description is normalized for any scale; linear flow rates listed are independent of column diameter, loading ratios are in mass per unit column volume. Examples are provided for the operation and the recovery at 1 gram, 40 gram, and 125 gram scales. (Examples IA–ID).

Purification Process Description

Removal of Cells from Culture

To harvest the culture fluid, the cells are removed using a tangential-flow microfiltration device (Prostak) equipped with a 0.65 micron filter or equivalent. The product is recovered in the permeate. For small volume cultures, centrifugation can be used.

Affinity Capture by Protein A Chromatography

The IgG is recovered from the CCF by adsorption chromatography on a column of ProSep A (BioProcessing Ltd.) previously equilibrated with PBS. The medium is applied to the column at a flow rate up to 1000 cm/hr at a load ratio of up to 15 grams IgG per liter column volume. After loading the column, it is washed with at least 3 column volumes of PBS containing 0.1 M glycine. The RSHZ-19 is eluted with a low pH buffer by applying approximately 3 column volumes of Elution Buffer.

The Protein A chromatography removes a large proportion of cell and media derived impurities (particularly protein and DNA in the flow-through and wash fractions), and concentrates RSHZ- 19 in the elution buffer for further processing.

Viral Inactivation at Acid pH (Optional)

The Protein A column eluate is collected and adjusted to pH 3.5 by the addition of 2.5M HCl. The solution is transferred to a second vessel and held at pH 3.5 for at least thirty minutes to provide viral inactivation, and readjusted to pH 5.5 by the addition of Tris buffer. The resulting solution is filtered through a prefilter (Millipore Polygard or equivalent) and a sterilized 0.2 μm filter (Millipore Millipak or equivalent), and held in sterile containers at 4° C., or frozen and held at −70° C.

The pH 3.5 treatment provides viral inactivation, and the pH 5.5 adjustment prepares the solution for cation exchange chromatography (CEC). The pH 3.5 treatment can be omitted if desired.

Cation Exchange Chromatography

The pH inactivated Protein A eluate is further purified by CEC chromatography on column of CM SEPHAROSE FF (Pharmacia LKB). The sample is applied to the equilibrated column at a flow rate of 150 cm/hr and a load ration of ≦20 grams protein per liter CM SEPHAROSE. After loading, the column is washed with 3 to 5 column volumes of Equilibration Buffer. The product is eluted with 3–5 column volumes of Elution Buffer.

The cation exchange chromatography step removes protein and non-protein impurities.

Viral Inactivation with Guanidine

The cation exchange eluate is adjusted to approximately 2.0M guanidine hydrochloride by the slow addition (with mixing) of one-half volume of Guanidine Stock Solution. The rate of reagent addition is adjusted so that it is added over a 5–15 minute period. The solution is transferred to a second vessel, and is held for thirty minutes to achieve viral inactivation. After holding, an equal volume of Ammonium Sulfate Stock Solution is slowly added (with mixing), and the hydrophobic interaction chromatography (HIC) step is performed immediately. The rate of reagent addition is adjusted so that it is added over a 5–15 minute period.

The guanidine treatment provides a second viral inactivation step, when an acid inactivation step is employed, and keeps the RSHZ-19 soluble after ammonium sulfate addition; the addition of ammonium sulfate serves to dilute the guanidine and prepare the solution for HIC.

Hydrophobic Interaction Chromatography

The guanidine-treated solution is further purified by application to an HIC column consisting of TOYO-PEARL Phenyl-650M previously equilibrated with Equilibration Buffer. The guanidine-treated solution is applied to the column at a flow rate of 150 cm/hr and a load ratio of ≦20 grams protein per liter Phenyl-650M. After loading, the column is washed with 3 to 5 column volumes of Equilibration Buffer. A linear gradient of decreasing ammonium sulfate is applied at a flow rate of 100–150 cm/hr, and the RSHZ-19 elutes as one major peak with impurities eluting later in the gradient. The slope of the gradient is approximately 20 column volumes, starting at 10% Equilibration Buffer and ending at 100% Gradient Buffer (1.3 to 0M ammonium sulfate). The peak is collected until the absorbance decreases to 20% of the maximum peak absorbance, then collection of the product fraction is ended. After the gradient ends, the column is washed with approximately 3 column volumes of Strip Buffer.

The HIC chromatography step removes additional protein and non-protein impurities, most notably residual Protein A, IgG aggregates, and host DNA.

Concentration, Diafiltration and Final Filtration

The HIC elute is concentrated to approximately 10 milligram per milliliter using a tangential-flow ultrafiltration device (such as a Millipore CUF) outfitted with a 30,000 molecular weight cut-off filter, diafiltered into a suitable formulation buffer and filtered through a sterilized 0.2 micron filter (Millipore Millipak or equivalent) into sterilized containers.

In-Process Assays

Process intermediates are assayed for total protein concentration by OD280 or Bradford assay, RSHZ-19 concentration by HLPC, sodium dodecyl sulfate polyacrylamide gel electrophoresis (SDS-PAGE). Aggregated product is assessed by size exclusion HPLC on TSK3000 SWXL, and Protein A residue is assayed using an ELISA.

Pooling Criteria

The eluate fractions from the Protein A capture and cation exchange steps are pooled based on the UV tracing on the chromatogram, and the entire peak is collected. The eluate from the HIC step is pooled based on the UV tracing, and the main peak is pooled until the UV reading on the tailing side of the peak reaches 20% of the peak maximum. The HIC tail fraction contains the majority of the Protein A and aggregated IgG's.

TABLE 1

Buffer Formulations

| Buffer Name | Composition |
|---|---|
| PBS | 20 mM sodium phosphate. 150 mM sodium chloride, pH 7 |
| PBS/glycine | PBS plus 0.1M glycine |
| ProSep Elution Buffer | 25 mM citrate, pH 3.5 |
| CM SEPHAROSE Equilibration Buffer | 10 mM citrate, pH 5.5 |
| CM SEPHAROSE Elution Buffer | 40 mM citrate, 100 mM sodium chloride, pH 6 |
| Guanidine Stock Solution | 6M guanidine hydrochloride, 50 mM sodium phosphate, pH 7 |
| 2.6M Ammonium Sulfate Stock Solution | 2.6M ammonium sulfate, 50 mM sodium phosphate, pH 7 |
| 2.0M Ammonium Sulfate Stock Solution | 2.0M ammonium sulfate, 50 mM sodium phosphate, pH 7 |
| Phenyl-650 Equilibration Buffer | 1.3M ammonium sulfate, 50 mM sodium phosphate, pH 7 |
| Phenyl-650 Gradient Buffer | 50 mM sodium phosphate, pH 7 |
| Butyl-650 Equilibration Buffer | 1.0M ammonium sulfate, 50 mM sodium phosphate, pH 7 |
| Butyl-650 Gradient Buffer | 50 mM sodium phosphate, pH 7 |
| HIC Strip Buffer | 0.2M NaOH |

Example IA. RSHZ-19 Purification at 1 Gram Scale Using TOYOPEARL Phenyl-650M

A 5.0 liter (20 cm diameter by 16 cm length) ProSep A affinity column was equilibrated with PBS (see Table 1) at 5.2 liter/min. 100 liters of conditioned culture medium containing 0.8 grams per liter of RSHZ-19 monoclonal antibody was clarified by microfiltration as described above, and applied to the column at a flow rate of 5.2 liter/min. After the load, approximately 15 liters of PBS/glycine was applied to the column at the same flow rate. The IgG was eluted by applying 15–20 liters of ProSep A elution buffer. Fractions of the non-bound peak and the elution peak were collected and assayed for IgG content using an HPLC assay. The eluate was approximately 15 liters in volume, and contained approximately 5 milligrams protein per milliliter.

Immediately after elution, the sample was adjusted to pH 3.5 by the addition of 2.5M hydrochloric acid, held for approximately 30 minutes, and adjusted to pH 5.5 by the addition of approximately 350 milliliters of 1M Tris base. After neutralizing to pH 5.5, the sample was filtered through a 0.1 micron Polygard CR filter in tandem with a sterile 0.2 micron Millipak 200, into a sterile container. The filtrate was stored at 4° C. Samples of the filtrate were analyzed for IgG content using an HPLC assay, and for total protein by absorbance at 280 nanometers. The samples were also analyzed for Protein A content by an ELISA procedure. This pH 3.5 treated and filtered Prosep A eluate was used as the CM SEPHAROSE load in Examples IA, B and C.

400 milliliters of pH 3.5 treated and filtered ProSep A eluate were loaded directly onto a 220 milliliter (4.4 cm diameter × 15 cm length) column of CM SEPHAROSE FF at 38 mL/min, which had been previously equilibrated with CM Equilibrated buffer. After loading, the column was washed at 38 mL/min with approximately 700 milliliters of CM Equilibration Buffer. The IgG was eluted by applying CM Elution Buffer at 38 mL/min. The IgG came off the column after approximately 1 bed volume of Elution Buffer had passed. The entire peak was collected as CM SEPHAROSE eluate. Fractions of the CM non-bound, eluate and strip fractions were collected and analyzed for IgG content, total protein content, and Protein A content as described previously. The eluate was approximately 160 milliliters in volume, and contained approximately 12 milligrams protein per milliter. This CM SEPHAROSE eluate was split into two equal portions of approximately 80 milliliters, and was used in Examples IA and IB for the HIC load.

To 80 milliliters of CM SEPHAROSE eluate was added (slowly with constant stirring) a total of 40 milliliters of Guanidine Stock Solution. This brought the guanidine concentration to 2M for viral inactivation. While stirring the guanidine-treated solution, a total of 120 milliliters of 2.6M Ammonium Sulfate Stock Solution was added. The resulting solution was 1.0M in guanidine and 1.3M in ammonium sulfate. The ammonium sulfate treated solution was applied to an 80 mL column (3.2 cm diameter × 10 cm length) of TOYOPEARL Phenyl-650M, previously equilibrated with Phenyl Equilibration Buffer. The flow rate was 20 mL/min throughout the run. After loading, the column was washed with approximately 350 milliliters of Phenyl Equilibration Buffer. The IgG was eluted by applying a linear gradient starting at 85% Equilibration/15% Gradient buffer and ending at 0% Equilibration/100% Gradient buffer, in 18–19 column volumes. This represents a starting ammonium sulfate concentration of approximately 1.1M and an ending concentration of 0M. The slope of this gradient was approximately a 4.7% increase in elution buffer per column volume, or −0.061M ammonium sulfate per column volume. The IgG began to elute from the column at approximately 7 column volumes and ended at approximately 13 column volumes into the gradient (ammonium sulfate concentration of approximately 0.7 to 0.3M). The eluted fraction was collected until the UV absorbance on the tailing side of the peak decreased to 20% of the peak height, then collection was switched to another vessel (tail fraction). At the end of the gradient, approximately 250 mL of HIC Strip Buffer was applied to regenerate the column. Fractions of the Phenyl non-bound, eluate, tail and strip fractions were collected and analyzed for IgG content, total protein content, and Protein A content as described previously. The eluate was approximately 300 milliliters in volume, and contained approximately 2.4 milligrams protein per milliter.

Table 2 summarizes the column parameters for this example. The product and protein recovery data for each step are shown in Table 3, along with the Protein A content, expressed as nanograms Protein A per milligram IgG (ng/mg). As seen in Table 3, the Protein A reduction over Phenyl-650M is approximately 4-fold, and the recovery is approximately 94%.

TABLE 2

Column Parameters at 1 gram scale using Phenyl-650M

| Step | Column Volume (liter) | Column dia × length (cm) | Load Ratio | Flow Rates (cm/hr) | Flow Rates (mL/min) |
|---|---|---|---|---|---|
| ProSep A | 5.0 | 20 × 16 | 16.0 g IgG per liter bed volume | 1000 | 5200 |
| CM SEPHAROSE FF | 0.22 | 4.4 × 15 | 9.1 g protein per liter bed volume | 150 | 38 |
| Phenyl-650M | 0.08 | 3.2 × 10 | 10.4 g protein per liter bed volume | 150 | 20 |

TABLE 3

Purification Summary for Example IA, 1 gram scale using Phenyl-650M

| Step | Volume (Liters) | Total RSHZ-19[a] (Grams) | Total Protein[b] (Grams) | Step Yield (%) | Protein A[c] (ng/mg) |
|---|---|---|---|---|---|
| Cell-free Culture Fluid | 100 | 80.3 | n.d. | — | 0 |
| ProSep A Eluate | 15.8 | 73.8 | 80.4 | 92 | 20.2 |
| CM SEPHAROSE[d] Load | (0.4)[d] | (1.87)[d] | (2.04)[d] | | |
| CM SEPHAROSE Eluate | 0.16 | 2.01 | 1.88 | 100 | 14.5 |
| Phenyl-650M[d] Load | (0.21)[d] | (0.72)[d] | (0.83)[d] | | |
| Phenyl-650M Eluate | 0.31 | 0.68 | 0.73 | 94 | 3.5 |
| (Phenyl Tail | 0.59 | 0.075 | 0.10 | — | 133)[e] |
| Cumulative Recovery (%) | | | | 86 | |

[a]by HPLC
[b]by Absorbence at 280 nm ÷ 1.27 mL $mg^{-1}$ $cm^{-1}$
[c]by ELISA
[d]Only a portion of the total eluate from the previous column was carried forward, as described in the text above
[e]Protein A migrates primarily in the Tail fraction Example IB. RSHZ-19 Purification at 1 Gram Scale Using TOYOPEARL Butyl-650M This preparation used the same CM SEPHAROSE eluate as described in Example IA, and the HIC step was performed using TOYOPEARL Butyl-650M instead of Phenyl-650M. The preparation of the CM SEPHAROSE eluate is described in Example IA above. To 80 milliliters of CM SEPHAROSE eluate was added (slowly with constant stirring) a total of 40 milliliters of Guanidine Stock Solution. This brought the guanidine concentration to 2M for viral inactivation. While stirring the guanidine-treated solution, a total of 120 milliliters of 2.0M Ammonium Sulfate Stock Solution was added. The resulting solution was 1.0M in guanidine and 1.0M in ammonium sulfate. The ammonium sulfate treated solution was applied to a an 80 mL column (3.2 cm diameter × 10 cm length) of TOYOPEARL Butyl-650M, previously equilibrated with Butyl Equilibration Buffer. The flow rate was 20 mL/min throughout the run. After loading, the column was washed with approximately 350 milliliters of Butyl Equilibration Buffer. The IgG was eluted by applying a linear gradient starting at 65% Equilibration/35% Gradient buffer and ending at 20% Equilibration/80% Gradient buffer, in 12–13 column volumes. This represents a starting ammonium sulfate concentration of approximately 0.65M and an ending concentration of approximately 0.2M. The slope of this gradient was approximately a 3.3% increase in elution buffer per column volume, or −0.033M ammonium sulfate per column volume. The IgG began to elute from the column at approximately 2 column volumes and ended at approximately 9 column volumes into the gradient (ammonium sulfate concentration of approximately 0.58 to 0.35M). The eluate fraction was collected until the UV absorbance on the tailing side of the peak decreased to 10% of the peak height, then collection was switched to another vessel. At the end of the gradient, approximately 250 mL of Butyl Gradient Buffer was applied, and a small peak eluted and was collected. Approximately 250 mL of HIC Strip Buffer was applied to regenerate the column. Fractions of the Butyl non-bound, eluate, tail and strip fractions were collected and analyzed for IgG content, total protein content, and Protein A content as described previously. The eluate was approximately 400 milliliters in volume, and contained approximately 1.5 milligrams protein per milliter.

Table 4 summarizes the column parameters for this example. The product and protein recovery data for each step are shown in Table 5, along with the Protein A content, expressed as nanograms Protein A per milligram IgG (ng/mg). Although the recovery of IgG is lower compared to Example IA (79% v. 94%), the Protein A content is reduced approximately 20-fold using Butyl-650M as an HIC step.

TABLE 4

Column Parameters at 1 gram scale using Butyl-650M

| Step | Column Volume (liter) | Column dia × length (cm) | Load Ratio | Flow Rates (cm/hr) | Flow Rates (mL/min) |
|---|---|---|---|---|---|
| CM SEPHAROSE FF | 0.22 | 4.4 × 15 | 9.1 g protein per liter bed volume | 150 | 38 |
| Butyl-650M | 0.08 | 3.2 × 10 | 10.4 g protein per liter bed volume | 150 | 20 |

TABLE 5

Purification Summary for Example IB, 1 gram scale using Butyl-650M

| Step | Volume (Liters) | Total RSHZ-19[a] (Grams) | Total Protein[b] (Grams) | Step Yield (%) | Protein A[c] (ng/mg) |
|---|---|---|---|---|---|
| Cell-free Culture Fluid | 100 | 80.3 | n.d. | — | 0 |
| ProSep A Eluate | 15.8 | 73.8 | 80.4 | 92 | 20.2 |
| CM SEPHAROSE[d] Load | (0.4)[d] | (1.87)[d] | (2.04)[d] | | |
| CM SEPHAROSE Eluate | 0.16 | 2.01 | 1.88 | 100 | 14.5 |
| Butyl-650M[d] Load | (0.21)[d] | (0.72)[d] | (0.86)[d] | | |
| Butyl-650M Eluate | 0.41 | 0.60 | 0.62 | 79 | 0.7 |
| (Butyl Tail | 0.40 | 0.03 | 0.03 | — | 31.4)[e,f] |
| (Butyl Strip | 0.53 | 0.10 | 0.10 | — | n.d.)[g] |
| Cumulative Recovery | 73 | | | | |
| Mass Balance (% of load) | | | | 95 | |

[a]by HPLC
[b]by Absorbence at 280 nm ÷ 1.27 mL $mg^{-1}$ $cm^{-1}$
[c]by ELISA
[d]Only a portion of the total eluate from the previous column was carried forward, as described above
[e]Protein A migrates primarily in the Tail fraction
[f]Tail contains 3% of the load
[g]strip contains 13% of the protein that was loaded Example IC. RSHZ-19 Purification at 40 Gram Scale Using TOYOPEARL Phenyl-650M This preparation used the same ProSep A eluate as described in Example IA, and the downstream steps were scaled-up to accomodate approximately 40 grams of protein, using TOYOPEARL Phenyl-650M as the HIC medium. The preparation of the CM SEPHAROSE Load is described in Example IA above. 7.8 liters of pH 3.5 treated and filtered ProSep A eluate were loaded directly onto a 4.2 liter (25 cm diameter × 8.5 cm length) column of CM SEPHAROSE FF which had been previously equilibrated with CM Equilibration buffer at 1.2 L/min. After loading, the column was washed at 1.2 L/min with approximately 8 liters of CM Equilibration Buffer. The IgG was eluted by applying CM Elution Buffer at 1.2 L/min. The IgG came off the column after approximately 1 bed volume of Elution Buffer had passed. The entire peak was collected as CM SEPHAROSE eluate. The column fractions of the CM non-bound and eluate were collected and analyzed for IgG content, total protein content, and Protein A content as described previously. The eluate was approximately 5.7 liters in volume, and contained approximately 6–7 milligrams protein per milliter.

To 5.6 liters of CM SEPHAROSE eluate was added (slowly with constant stirring) a total of 2.8 liters of Guanidine Stock Solution (3.2 kilogram by weight). This brought the guanidine concentration to 2M for viral inactivation, at a volume of 8.3 liters. While stirring ring the guanidine-treated solution, a total of 8.3 liters (9.7 kg by weight) of 2.6M Ammonium Sulfate Stock Solution was added. The resulting solution was 1.0M in guanidine and 1.3M in ammonium sulfate, with a final volume of 16.7 liters. The ammonium sulfate treated solution was applied to a 4.6 liter column (18 cm diameter × 18 cm length) to TOYOPEARL Phenyl-650M, previously equilibrated with Phenyl Equilibration Buffer. The flow rate was 0.5–0.6 L/min throughout the run. After loading, the column was washed with approximately 14 liters of Phenyl Equilibration Buffer. The IgG was eluted by applying a linear gradient starting at 100% Equilibration Buffer and ending at 100% Gradient buffer, in 20 column volumes. This represents a starting ammonium sulfate concentration of approximately 1.3M and an ending concentration of 0M. The slope of this gradient was approximately a 5% increase in elution buffer per column volume, or −0.065M ammonium sulfate per column volume. The IgG began eluting from the column at approximately 7 column volumes and ended at approximately 12 column volumes into the gradient (ammonium sulfate concentration of approximately 0.85 to 0.5M). The eluate fraction was collected until the UV absorbance on the tailing side of the peak decreased to 20% of the peak height, then collection was switched to another vessel (tail). Fractions of the Phenyl non-bound, eluate and tail and strip fractions were collected and analyzed for IgG content, total protein content, and Protein A content as described previously. The eluate was approximately 15.4 L in volume, and contained approximately 2.2 milligrams protein per milliter.

The Phenyl Eluate was concentrated to approximately 16 mg/mL using a tangential flow ultrafiltration apparatus (CUF, Millipore Corp.) equipped with 30,000 MWCO Omega membranes (Filtron Corp.) and buffer exchanged by continuous diafiltration against a suitable formulation buffer.

Table 6 summarizes the column parameters for this example. The product and protein recovery data for each step are shown in Table 7, along with the Protein A content, expressed as nanograms Protein A per milligram IgG (ng/mg) and the IgG aggregate content, expressed as % of total IgG. As seen in Table 7, the Protein A reduction over Phenyl-650M is approximately 3-fold, and the recovery is approximately 90%. IgG aggregates were reduced from 0.5% in the CM SEPHAROSE eluate to 0.06% in the formulated product.

TABLE 6

| Column Parameters at 40 gram scale | | | | | |
|---|---|---|---|---|---|
| Step | Column Volume (liter) | Column dia × length (cm) | Load Ratio | Flow Rates (cm/hr) | Flow Rates (L/min) |
| CM SEPHAROSE FF | 4.2 | 25 × 8.5 | 8.9 g protein per liter bed volume | 150 | 1.2 |
| Phenyl-650M | 4.6 | 18 × 18 | 10.4 g protein per liter bed volume | 140 | 0.6 |

TABLE 7

| Purification Summary for Example IC: 40 gram scale | | | | | | |
|---|---|---|---|---|---|---|
| Step | Volume (Liters) | Total RSHZ-19[a] (Grams) | Total Protein[b] (Grams) | Step Yield (%) | Protein A[c] (ng/mg) | IgG Aggregate (%) |
| Cell-free Culture Fluid | 100 | 80.3 | n.d. | — | 0 | n.d. |
| ProSep A Eluate | 15.8 | 73.8 | 80.4 | 92 | 20.2 | n.d. |
| CM SEPHAROSE[d] Load | (7.84)[d] | (36.0)[d] | (37.3)[d] | | | |
| CM SEPHAROSE Eluate | 5.71 | 36.5 | 37.3 | 100 | 21.4 | 0.5% |
| Phenyl-650M Eluate (Product) | 15.4 | 32.8 | 33.6 | 90 | 8.0 | <0.05 |
| Phenyl Tail | 24.6 | 2.5 | 3.0 | — | 78.0 | 5.1)[e] |
| Formulated Product | 2.0 | 32.8 | 32.0 | 100 | 6.5 | 0.06 |
| Cumulative Recovery (%) | | | | 83 | | |
| Mass Balance (% of load) | | | | 97 | | |

[a]by HPLC
[b]by Absorbence at 280 nm ÷ 1.27 mL $mg^{-1}$ $cm^{-1}$
[c]by ELISA
[d]Only a portion of the total ProSep A Eluate was carried forward
[e]Protein A and IgG aggregates migrate primarily in the tail fraction Example ID. RSHZ-19 Purification at 125 Gram Scale Using TOYOPEARL Phenyl-650M A 5.5 liter (20 cm diameter by 18 cm length) ProSep A affinity column was equilibrated with PBS (see Table 1) at 4.8 liter/min. 450 liters of conditioned culture medium containing 0.94 grams per liter of RSHZ-19 monoclonal antibody was clarified by microfiltration as described above, and applied in four separate 90–95 liter portions and one 40 liter portion to the column at a flow rate of 4.8 liter/min (and so throughout). Each cycle on the column ran as follows: After the load, approximately 17 liters of PBS/glycine was applied to the column at the same flow rate. The IgG was eluted by applying 15–20 liters of ProSep A Elution buffer. Fractions of the non-bound peak and the elution peak were collected and assayed for IgG content using an HPLC assay. The eluate from each cycle was approximately 9 liters in volume, and contained approximately 5–10 milligrams protein per milliliter. Immediately after elution, the ProSep A eluates were adjusted to pH 3.5 by the addition of 2.5M hydrochloric acid, held for approximately 30 minutes, and adjusted to pH 5.5 by the addition of approximately 250 milliliters of 1M Tris base. After neutralizing to pH 5.5, the eluates were pooled together, and filtered through a 0.1 micron Polygard CR filter in tandem with a sterile 0.2 micron Millipak 200, into 5 liter aliquots in sterile containers. The filtrate was stored at 4° C. Samples of the filtrate were analyzed for IgG content using an HPLC assay, and for total protein by absorbance at 280 nanometers. The samples were also analyzed for Protein A content by an ELISA procedure, and IgG aggregates by HPLC.

To downstream steps were scaled-up to accommodate approximately 120–140 grams of protein. 16.3 liters of pH 3.5 treated and filtered ProSep A eluate containing approximately 130 grams of protein was loaded directly onto a 14.4 liter (35 cm diameter × 15 cm length) column of CM SEPHAROSE FF at 2.4 L/min, which had been previously equilibrated with CM Equilibration buffer. After loading, the column was washed at 2.4 L/min with approximately 45 liters of CM Equilibration Buffer. The IgG was eluted by applying CM Elution Buffer at 2.4 L/min. The IgG began to elute from the column after approximately 1–2 bed volumes of Elution Buffer had passed. The entire peak was collected as CM SEPHAROSE eluate. Fractions of the CM non-bound and eluate were collected and analyzed for IgG content, total protein content, and IgG aggregate. The eluate was approximately 21 liters in volume, and contained approximately 120 grams protein.

To 19.4 liters of CM SEPHAROSE eluate was added (slowly with constant stirring) a total of 9.7 liters of Guanidine Stock Solution. This brought the guanidine concentration to 2M for viral inactivation, at a volume of 29.1 liters. While stirring the guanidine-treated solution, a total of 29.1 liters of 2.6M Ammonium Sulfate Stock Solution was added. The resulting solution was 1.0M in guanidine and 1.3M in ammonium sulfate, with a final volume of 58.2 liters. The ammonium sulfate treated solution was applied to a 12.4 liter column (30 cm diameter × 18 cm length) of TOYOPEARL Phenyl-650M, previously equilibrated with Phenyl Equilibration Buffer. The flow rate was 1.1–1.3 L/min throughout the run. After loading, the column was washed with approximately 37 liters of Phenyl Equilibration Buffer. The IgG was eluted by applying a linear gradient starting at 80% Equilibration Buffer/20% Gradient Buffer and ending at 20% Equilibration Buffer/80% Gradient buffer, in 12 column volumes. This represents a starting ammonium sulfate concentration of approximately 1.0M and an ending concentration of approximately 0.26M. The slope of this gradient was approximately a 5% increase in Gradient buffer per column volume, or –0.065M ammonium sulfate per column volume. The IgG came off the column essentially in the middle of the gradient, with the peak containing approximately 0.8M ammonium sulfate. The eluate fraction was collected until the UV absorbance on the tailing side of the peak decreased to 20% of the peak height, then collection was switched to another vessel (tail). Fractions of the Phenyl non-bound, eluate and tail and strip fractions were collected and analyzed for IgG content, total protein content, and IgG aggregate. The eluate was approximately 29 L in volume, and contained approximately 100 grams protein.

TABLE 8

Column Parameters at 125 gram scale

| Step | Column Volume (liter) | Column dia × length (cm) | Load Ratio | Flow Rates (cm/hr) | Flow Rates (L/min) |
|---|---|---|---|---|---|
| ProSep A | 5.0 | 20 × 18 | 14-16 g RSHZ-19 per liter bed volume | 915 | 4.8 |
| CM SEPHAROSE FF | 14.4 | 35 × 15 | 8.4 g protein per liter bed volume | 150 | 2.4 |
| Phenyl-650M | 12.4 | 30 × 18 | 8.6 g protein per liter bed volume | 100 | 1.2 |

TABLE 9

Purification Summary for Example ID: 125 gram scale

| Step | Volume (Liters) | Total RSHZ-19[a] (Grams) | Total Protein[b] (Grams) | Step Yield (%) | Protein A[c] (ng/mg) | IgG Aggregate (%) |
|---|---|---|---|---|---|---|
| Cell-free Culture Fluid | 416 | 392 | 477[C] | — | 0 | n.d. |
| ProSep A Eluate | 48.7 | 375 | 384 | 96 | 11.7 | 0.4 |
| CM SEPHAROSE[d] Load | (16.3)[d] | (125)[d] | (129)[d] | — | | |
| CM SEPHAROSE Eluate | 20.6 | 116 | 117 | 93 | n.d. | 0.4 |
| Phenyl-650M Eluate | 29.1 | 98.1 | 99.8 | 85 | n.d. | <0.05 |
| Formulated Product | 9.29 | 89.8 | 91.1 | 92 | 1.7 | 0.06 |
| Cumulative Recovery (%) | | | | 70 | | |

[a]by Reversed-Phase HPLC
[b]by Absorbence at 280 nm ÷ 1.27 mL $mg^{-1}$ $cm^{-1}$
[c]by Bradford assay
[d]Downstream process capacity is approximately 140 grams; only a portion of the total ProSep A eluate is carried forward The Phenyl Eluate was concentrated to approximately 10 mg/mL using a tangential flow ultrafiltration apparatus (CUF, Millipore Corp.) equipped with 30,000 MWCO Omega membranes (Filtron Corp.) and buffer exchanged by continuous diafiltration against a suitable formulation buffer. The product was analyzed for IgG content, total protein, Protein A and IgG aggregate.

Table 8 summarizes the column parameters for this example. The product and protein recovery data for each step are shown in Table 9, along with the Protein A content, expressed as nanograms Protein A per milligram IgG (ng/mg) and the IgG aggregate content, expressed as % of total IgG. As seen in Table 9, the Protein A reduction over CM SEPHAROSE and Phenyl-650M is approximately 7-fold, and the cumulative recovery is approximately 70%. IgG aggregates were reduced from 0.4% in the CM SEPHAROSE eluate to 0.06% in the formulated product.

TABLE 10

Purity analysis: 125 Gram Scale

| Step | Aggregates (% of Total IgG) | Purity[a] (% of Total Area) | Activity[b] (%) |
|---|---|---|---|
| CCF | not applicable | not done | 80[c] |
| ProSep Eluate | 0.4 | 98.5 | 105 |
| CM Eluate | 0.4 | 98.4 | 109 |
| Phenyl Eluate | <0.05 | 98.3 | 99 |
| Final product | 0.06 | 99.7 | 115 |

[a]Determined by scanning densitometry of reducing SDS-PAGE; sum of area of Heavy and Light chains of IgG
[b]Calculated ratio of activity (determined by Bovine RS Virus binding ELISA) to RSHZ-19 concentration (determined by A280)
[c]Calculated ratio of activity, by bovine RS virus ELISA, to RSHZ-19 concentration by HPLC

EXAMPLE II

The anti-CD4 monoclonal antibody CH-CD14 was made by cell culture techniques and partially purified using Protein A and ion exchange chromatography in a fashion similar to that used in Example I, except that an anion exchange resin was employed. An Amicon column (1 cm diameter by 10 cm high) was packed with 8 mL of Phenyl TOYOPEARL 650M resin (lot #65PHM01 H). The flow rate was maintained at 2 mL/min for all steps. The column was equilibrated with 20 mL Equilibration buffer (1M ammonium sulfate, 50 mM sodium phosphate, pH 7.0). The product was prepared for loading on the column by taking 5 mL partially purified CH-CD4 monoclonal antibody (17 mg/mL concentration by absorbance at 280 nm), adding 2.5 mL 6M guanidine HCl, 50 mM sodium phosphate, pH 7.0, mixing, holding for 30 minutes, and then adding 7.5 mL 2M ammonium sulfate, 50 mM sodium phosphate, pH 7.0. The final ammonium sulfate concentration of the load was 1 M, the final guanidine HCl concentration was 1M, the final volume after samples were taken was 12 mL, and the final concentration of product was 5.6 mg/mL. This material was then loaded on the column at 2 mL/min and then eluted with a 10 column volume linear gradient of Equilibration buffer to 50 mM sodium phosphate, pH 7.0. Fractions of approximately 4 mL were taken as the product eluted from the column.

The results are shown in Table 11. All of the product eventually eluted in the gradient. Protein A also eluted and was enriched in later fractions from the gradient. To achieve a reduction in Protein A in the final product, it was necessary to exclude some of the fractions at the end of the gradient, thus reducing the yield of product. A two-fold reduction in Protein A was possible with an 86% yield of product and a three-fold reduction was possible with a 50% yield.

TABLE 11

| Fraction No. | Volume (mL) | Product (mg/mL) | Protein A (ng/mL) | Cumulative Specific Protein A (ng/mg) | Cumulative Product Yield | Protein A Removal Factor[a] |
|---|---|---|---|---|---|---|
| 0 | Load 12 Eluate | 5.8 | 200.7 | 35 | | |
| 1 | 5.5 | 0.04 | 0.0 | 0 | 0% | |
| 2 | 3 | 0.31 | 0.0 | 0 | 2% | |
| 3 | 4.2 | 1.32 | 6.4 | 4 | 10% | 8.6 |
| 4 | 4.2 | 3.1 | 16.9 | 5 | 28% | 7.0 |
| 5 | 4 | 4 | 68.3 | 10 | 51% | 3.3 |
| 6 | 4.2 | 3.4 | 80.9 | 14 | 72% | 2.4 |
| 7 | 4.2 | 2.3 | 94.1 | 19 | 86% | 1.9 |
| 8 | 4.2 | 1.3 | 79.3 | 22 | 94% | 1.6 |
| 9 | 4.2 | 0.71 | 49.9 | 24 | 98% | 1.4 |
| 10 | 4.2 | 0.36 | 32.8 | 26 | 100% | 1.3 |
| 11 | 4 | 0.19 | 22.9 | 27 | 101% | 1.3 |
| 12 | 4 | 0.11 | 13.5 | 27 | 102% | 1.3 |
| 13 | 9.6 | 0.05 | 8.5 | 28 | 102% | 1.2 |

[a]Removal factor is calculated by pooling eluate fractions from start of eluate to desired fraction and dividing initial Protein A in load by Protein A ng/mg in pooled eluate fractions. For example, the factor 8.6 is calculated by dividing the sum of Protein A in fractions 1-3 by the sum of product in fractions 1-3 to get ng/mg. This number is then divided by 35 ng/mg in the load to obtain 8.6.

EXAMPLE IIB:

CH-CD4 monoclonal antibody was partially purified, and prepared for loading on the HIC column as described in example IIA. The same column, flowrate, equilibration and loading described in example IIA were used. In this example, after the column was loaded and washed with Equilibration buffer, it was washed with 18 mL Wash buffer (1M ammonium sulfate, 50 mM sodium citrate, pH 3.5). This was followed by another washing with 13.5 mL Equilibration buffer described in example IIA). The column was eluted with a gradient and then washed with water as described in example IIA. The column eluate was divided into 14 mL fractions which were then analyzed for product and Protein A.

The results are presented in Table 12. Protein A could be reduced by 6 fold at 90% yield, and by 8 fold at 78% yield.

TABLE 12

| Fraction No. | Volume (mL) | Product (mg/mL) | Protein A (ng/mL) | Cumulative Specific Protein A (ng/mg) | Cumulative Product Yield | Protein A Removal Factor[1] |
|---|---|---|---|---|---|---|
| 0 | Load 12 Eluate | 5.80 | 167.1 | 29 | | |
| 1 | 14 | 1.50 | 0 | 0.0 | 30% | — |
| 2 | 14 | 2.35 | 13.6 | 3.5 | 78% | 8.1 |

TABLE 12-continued

| Fraction No. | Volume (mL) | Product (mg/mL) | Protein A (ng/mL) | Cumulative Specific Protein A (ng/mg) | Cumulative Product Yield | Protein A Removal Factor[1] |
|---|---|---|---|---|---|---|
| 3 | 14 | 0.38 | 8.3 | 5.2 | 85% | 5.6 |
| 4 | 14 | 0.18 | 0 | 5.0 | 89% | 5.8 |
| 5 | 9 | 0.13 | 0 | 4.9 | 91% | 5.9 |

[1]As in footnote "a" to Table 11.

Comparing the results of example IIB with example IIA it can be seen that Protein A was reduced by 6 to 8 fold with about 80% yield when the pH 3.5 wash was included, but reduction was only about 2 fold with 80% yield of CH-CDH without the pH 3.5 wash.

EXAMPLE IIC:

This example was performed similar to example IIB, except that the scale was increased. Equilibration and Wash buffers are described in example IIB. The column was 5 cm in diameter and 28 cm high and the flowrate was 50 mL/min. CH-CD4 monoclonal antibody was prepared and partially purified, as described in example IIA. The partially purified product (440 mL) was mixed with 220 mL 6M guanidine HCl for 31 min. Then, 660 mL 2M ammonium sulfate, 50 mM sodium phosphate, pH 7.0 was added. The final ammonium sulfate concentration was 1M and the final antibody concentration was 5.3 mg/mL. After sampling, the load volume was 1,290 mL.

The column was equilibrated with 2 column volumes of Equilibration buffer and then loaded on the column. The column was then washed with 630 mL of Equilibration buffer, 1,000 mL of Wash buffer, 800 mL of Equilibration buffer, and then eluted with a 5 column volume gradient from 0.75M ammonium sulfate, 50 mM sodium phosphate, pH 7.0, to 50 mM sodium phosphate, pH 7.0. Fractions were collecting during elution.

The results are presented in Table 13. Protein A was reduced 100 fold with a yield of 70%, or by 30 fold with an antibody yield of 80%.

TABLE 13

| Fraction No. | Volume (mL) | Product (mg/mL) | Protein A (ng/mL) | Cumulative Specific Protein A (ng/mg) | Cumulative Product Yield | Protein A Removal Factor[a] |
|---|---|---|---|---|---|---|
| 0 | Load 1290 Eluate | 5.30 | 198 | 37 | | |
| 1 | 581 | 0.03 | 0 | 0.0 | 0% | |
| 2 | 304 | 3.60 | 0 | 0.0 | 16% | |
| 3 | 243 | 5.40 | 0 | 0.0 | 35% | |
| 4 | 238 | 4.50 | 0 | 0.0 | 51% | |
| 5 | 237 | 3.40 | 2.4 | 0.1 | 63% | 282 |
| 6 | 239 | 2.2 | 4.7 | 0.4 | 71% | 107 |
| 7 | 256 | 1.2 | 4.8 | 0.6 | 75% | 66 |
| 8 | 252 | 0.7 | 7.6 | 0.9 | 78% | 41 |
| 9 | 240 | 0.4 | 5.3 | 1.1 | 79% | 33 |
| 10 | 250 | 0.4 | 5.7 | 1.4 | 81% | 27 |
| 11 | 202 | 0.4 | 4.38 | 1.5 | 82% | 25 |
| 12 | 210 | 1 | 148.5 | 6.8 | 85% | 5 |

EXAMPLE IID

Partially purified CH-CD4 monoclonal antibody was prepared as shown in example IIA. Equilibration and Wash buffers are described in example IIB. Four milliliters of 6M guanidine HCl, 50 mM sodium phosphate, pH 7.0 was added to 8 mL of a 9.5 mg/mL solution of partially purified CH-CD4 monoclonal antibody and incubated for 30 minutes. Then, 12 mL of 2M ammonium sulfate, 50 mM sodium phosphate, pH 7.0 was added slowly. The column was 0.5 cm in diameter and 20 cm high (4 mL) and the flowrate for all steps was 0.5 mL/min. The column was rinsed with 2 column volumes each of water and Equilibration buffer. Then, 22 mL of the load solution was passed through the column, followed by 2 column volumes of Equilibration buffer, followed by Wash buffer until the pH of the column effluent was 3.5. This was followed by Equilibration buffer until the effluent pH was 7.0. The column was eluted with 0.3M ammonium sulfate, 50 mM sodium phosphate, pH 7.0. After the UV trace started to rise, 12.6 mL of eluate were collected and analyzed for product and Protein A. The yield of product was 80% and the Protein A was reduced was 28 ng/mg to 6 ng/mg, a reduction of 4.7 fold.

What is claimed is:

[1. A method for purifying monomeric IgG antibody from a mixture comprising said monomeric antibody and at least one of immunoglobulin aggregates, mis-folded species, host cell protein or protein A comprising contacting said mixture with a hydrophobic interaction chromatographic support and selectively eluting the monomer from the support.]

[2. The method according to claim 1 wherein the IgG is selected from the group consisting of anti-RSHZ-19 and CH-CD4.]

[3. The method according to claim 1 wherein the HIC support is selected from the group consisting of alkyl$_{C2-C8}$ agarose, aryl-agarose, alkyl-silica, aryl-silica alkyl organic polymer resin and aryl organic polymer resin.]

[4. The method according to claim 3 wherein the support is selected from the group consisting of butyl-, phenyl- and octyl-agarose and butyl-, phenyl- and ether- organic polymer resin.]

[5. The method according to claim 4 wherein the support is phenyl-organic polymer resin.]

[6. The method according to claim 4 wherein the support is butyl-organic polymer resin.]

[7. The method according to claim 1 wherein the antibody is selectively eluted with a low salt buffer.]

[8. The method according to claim 7 wherein the antibody is selectively eluted with a gradient decreasing in salt to 50 mM phosphate, pH7.0.]

[9. A method for the purification of an IgG antibody from conditioned cell culture medium containing same comprising sequentially subjecting the medium to (a) Protein A affinity chromatography, (b) ion exchange chromatography, and (c) hydrophobic interaction chromatography.]

10. [The method according to claim 9] *A method for the purification of an IgG antibody from conditioned cell culture medium containing same comprising sequentially subjecting the medium to (a) Protein A affinity chromatography, (b) ion exchange chromatography, and (c) hydrophobic interaction chromatography* wherein the ion exchange chromatography employs a support selected from the group consisting of [CM-23-, CM-32-, CM-52- cellulose; CM] *carboxymethyl-* and[, SP] *sulfopropyl*-cross-linked dextrans, [CM] *carboxymethyl-* and [S-argose] *sulfonate-agarose*; [CM] *carboxymethyl*-organic polymer resin; [DEAE-QAE-Q] *diethylaminoethyl-quaternary aminoethyl-quaternary amine*-cross-linked [dextians] *dextrans*; [DEAE-,QAE-,Q] *diethylaminoethyl-, quaternary aminoethyl-, quaternary amine*-linked agarose; and [DEAE] *diethylaminoethyl-*organic polymer resins and is [by a] buffered *by a* salt solution.

11. The method according to claim 10 wherein the support is [CM] *carboxymethyl*-agarose [Fast Flow] and the salt is NaCl.

12. The method according to claim 10 wherein the buffered salt solution is 40 mM citrate containing, 100 mM, NaCl, pH 6.0.

[13. The method according to claim 9 wherein the hydrophobic interaction chromatographic employs a support selected from the group consisting of alkyl$_{C2-C8}$-agarose, aryl-agarose, alkyl-silica, aryl-silica, alkyl-organic polymer resin and aryl-organic polymer resin.]

[14. The method according to claim 13 wherein the support is selected from the group consisting of butyl-, phenyl- and octyl-agarose and butyl-, phenyl- and ether-organic polymer resin.]

[15. The method according to claim 14 wherein the support is phenyl-organic polymer resin or butyl-organic polymer resin.]

[16. The method according to claim 9 wherein the support is phenyl- or butyl-organic polymer resin and the antibody is selectively eluted with a low salt buffer.]

[17. The method according to claim 16 wherein the antibody is selectively eluted with a gradient decreasing to 50 mM sodium phosphate buffer, pH 7.0.]

[18. The method according to claim 9 wherein the Protein A chromatography employs as a support Protein A linked to controlled pore glass and elution is by a low pH buffer.]

[19. The method according to claim 18 wherein said buffer is 25 mM citrate, pH 3.5.]

[20. A method for purifying antibody from a conditioned cell medium comprising:

(a) adsorbing the antibody onto a Protein A chromatographic support;

(b) washing the adsorbed antibody with at least one buffer;

(c) eluting the antibody from step (b);

(d) adsorbing the antibody from step (c) onto an ion exchange chromatographic support;

(e) washing the adsorbed antibody with at least one buffer;

(f) selectively eluting the antibody from step (e);

(g) adsorbing the eluate of step (f) onto a hydrophobic interaction chromatographic support;

(h) washing the adsorbed antibody with at least one buffer;

(i) eluting the adsorbed antibody; and (j) recovering the antibody.]

[21. The method according to claim 20 which includes one or more optional steps of inactivating viruses if present.]

[22. The method according to claim 21 wherein a viral inactivation step is performed after step (f) and before step (g).]

[23. The method according to claim 22 wherein said viral inactivation step comprises treatment of the eluate with guanidine hydrochloride for a period of time sufficient to inactivate virus followed by the addition of an ammonium sulfate solution.]

[24. The method according to claim 23 wherein the guanidine hydrochloride is present at 2.0M and following treatment eluate from step (f) is adjusted to 1.3M ammonium sulfate.]

[25. The method according to claim 22 wherein an additional viral inactivation step is performed after step (c) and before step (d).]

[26. The method according to claim 25 wherein said additional viral inactivation step comprises treatment of the eluate of step (c) with acid.]

[27. The method according to claim 26 wherein the pH of the eluate is adjusted to pH 3.5 and maintained at that pH for a period of time sufficient to inactivate virus, and terminating the treatment by adjusting the pH to 5.5.]

[28. The method according to claim 20 wherein the ion exchange support of step (d) is selected from the group consisting of carboxymethyl (CM), sulfoethyl (SE), sulfopropyl (SP), phosphate(P), diethylaminoethyl (DEAE), quaternary aminoethyl (QAE), and quarternary (Q), substituted cellulosic resins, cross linked dextrans, agarose and organic polymer resins.]

[29. The method according to claim 28 wherein the cationic support is CM-agarose.]

[30. The method according to claim 20 wherein the hydrophobic interaction chromatographic support is selected from the group consisting of alkyl $_{C2-C8}$-agarose, aryl-agarose, alkyl-silica, aryl-silica, alkyl-organic polymer resin and aryl-organic polymer resins.]

[31. The method according to claim 30 wherein the support is selected from the group consisting of butyl-, phenyl- and octyl-agarose and phenyl-, ether- and butyl-organic polymer resins.]

[32. The method according to claim 31 wherein the support is phenyl- or butyl-organic polymer resins.]

[33. The method according to claim 20 wherein said protein is recovered by pooling and concentrating the protein containing fractions from chromatography step (i) by ultrafiltration.]

[34. The method according to claim 20 wherein the chromatographic support of step (a) is Protein A linked to controlled pore glass.]

[35. The method according to claim 20 wherein the absorbed antibody of step (h) is washed with two buffers, a first equibration buffer and a second low pH wash buffer.]

[36. The method according to claim 35 wherein the pH of the second buffer is less than 4.0.]

[37. The method according to claim 36 wherein the second buffer is 1M ammonium sulfate, 50 mM sodium citrate, pH 3.5.]

[38. A method of removing Protein A from a mixture comprising Protein A and IgG antibodies comprising contacting the mixture with a hydrophobic interaction chromatography support and selectively eluting the antibody from the support.]

[39. The method according to claim 38 which includes washing the support prior to elution with a buffer having a pH less than 7.0.]

[40. The method according to claim 39 wherein the pH of the wash buffer is less than 4.0.]

[41. The method according to claim 40 wherein the buffer is (1M ammonium sulfate, 50 mM sodium citrate, pH 3.5).]

*42. A method for purifying monomeric IgG antibody from a mixture comprising said monomeric IgG antibody and at least one of immunoglobulin aggregates, misfolded species, and protein A, wherein said method comprises the steps of (i) contacting said mixture with a hydrophobic interaction chromatographic support and (ii) selectively eluting the monomeric IgG antibody from the support wherein the monomeric IgG antibody is selectively eluted with a low salt buffer gradient decreasing in salt to 50 mM phosphate, pH 7.0.*

* * * * *

UNITED STATES PATENT AND TRADEMARK OFFICE

CERTIFICATE OF CORRECTION

PATENT NO. : RE 41,595 E
APPLICATION NO. : 12/403799
DATED : August 31, 2010
INVENTOR(S) : Paula J. Shadle et al.

It is certified that error appears in the above-identified patent and that said Letters Patent is hereby corrected as shown below:

Title Page, Item 75

Inventors: Paula J. Shadle, (instead of Paul J. Shandle)

John C. Erickson, King of Prussia, PA, (instead of Research Triangle Park, NC)

Signed and Sealed this

Nineteenth Day of October, 2010

David J. Kappos

David J. Kappos
*Director of the United States Patent and Trademark Office*